(12) United States Patent
Bonnert

(10) Patent No.: US 7,585,867 B2
(45) Date of Patent: *Sep. 8, 2009

(54) SUBSTITUTED THIAZOLO[4,5-D]PYRIMIDIN-2(3H)-ONE

(75) Inventor: Roger Victor Bonnert, Loughborough (GB)

(73) Assignee: AstraZeneca AB, Södertälje (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/528,316

(22) PCT Filed: Sep. 16, 2003

(86) PCT No.: PCT/GB03/03998

§ 371 (c)(1),
(2), (4) Date: Dec. 1, 2005

(87) PCT Pub. No.: WO2004/026880

PCT Pub. Date: Apr. 1, 2004

(65) Prior Publication Data

US 2006/0100221 A1    May 11, 2006

(30) Foreign Application Priority Data

Sep. 20, 2002 (GB) ................... 0221828.7

(51) Int. Cl.
C07D 487/04 (2006.01)
A61K 31/519 (2006.01)
A61P 19/02 (2006.01)
A61P 19/10 (2006.01)
A61P 19/04 (2006.01)
A61P 11/16 (2006.01)
A61P 11/06 (2006.01)

(52) U.S. Cl. .................... 514/260.1; 544/255
(58) Field of Classification Search ............. 544/255; 514/260.1
See application file for complete search history.

(56) References Cited

U.S. PATENT DOCUMENTS

| 2,924,472 A | 2/1960 | Bush |
| 3,318,900 A | 5/1967 | Janssen |
| 3,445,120 A | 5/1969 | Barr |
| 4,061,459 A | 12/1977 | Parmann |
| 4,126,689 A | 11/1978 | Sanczuk et al. |
| 4,188,040 A | 2/1980 | Wolf et al. |
| 4,213,619 A | 7/1980 | Arlt et al. |
| 4,234,199 A | 11/1980 | Moncaster et al. |
| 4,278,677 A | 7/1981 | Nedelec et al. |
| 4,410,528 A | 10/1983 | Teranishi et al. |
| 4,483,544 A | 11/1984 | Faerber et al. |
| 4,641,858 A | 2/1987 | Roux |
| 5,064,207 A | 11/1991 | Bengtsson |
| 5,169,161 A | 12/1992 | Jones |
| 5,297,824 A | 3/1994 | Imhof et al. |
| 5,521,197 A | 5/1996 | Audia |
| 5,599,028 A | 2/1997 | Neumann et al. |
| 5,826,887 A | 10/1998 | Neumann et al. |
| 5,988,695 A | 11/1999 | Corbett, Jr. |
| 6,142,484 A | 11/2000 | Valls, Jr. |
| 6,172,067 B1 | 1/2001 | Ito et al. |
| 6,248,755 B1 | 6/2001 | Chapman et al. |
| 6,329,381 B1 | 12/2001 | Kurimoto et al. |
| 6,407,121 B1 | 6/2002 | Nagamine et al. |
| 6,432,981 B1 | 8/2002 | Finke et al. |
| 6,790,850 B1 | 9/2004 | Willis et al. |
| 6,790,854 B2 | 9/2004 | Tsushima et al. |
| 6,875,868 B2 | 4/2005 | Bonnert et al. |
| 6,949,643 B2 | 9/2005 | Bonnert |
| 6,958,343 B2 | 10/2005 | Bonnert et al. |
| 6,958,344 B2 | 10/2005 | Bonnert et al. |
| 7,071,193 B2 | 7/2006 | Bonnert et al. |
| 7,169,778 B2 | 1/2007 | Denny et al. |

(Continued)

FOREIGN PATENT DOCUMENTS

| DE | 2331223 | 1/1974 |
| DE | 41 19 767 A1 | 12/1992 |
| EP | 0 293 078 A1 | 11/1988 |
| EP | 0 447 324 A1 | 9/1991 |
| EP | 0 778 277 A1 | 6/1997 |
| EP | 1 069 124 B1 | 1/2001 |
| EP | 1 122 257 A1 | 8/2001 |
| EP | 1 348 709 B1 | 10/2003 |
| GB | 1009477 | 11/1965 |
| GB | 2359079 A | 8/2001 |
| JP | 51-88994 | 7/1993 |

(Continued)

OTHER PUBLICATIONS

Trivedi, B.K. et al, Ann. Reports Med. Chem., vol. 35, 2000, pp. 191-200.*

(Continued)

*Primary Examiner*—Brenda L Coleman
*Assistant Examiner*—Susanna Moore
(74) *Attorney, Agent, or Firm*—Fish & Richardson P.C.

(57) ABSTRACT

A compound of formula (I) and pharmaceutically acceptable salts or solvates thereof for use in therapy.

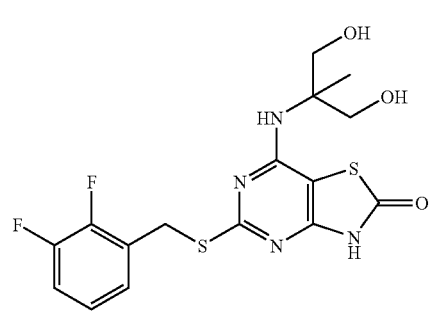

3 Claims, No Drawings

U.S. PATENT DOCUMENTS

| | | |
|---|---|---|
| 2003/0032642 A1 | 2/2003 | Bonnert et al. |
| 2003/0107189 A1 | 6/2003 | Bonnert et al. |
| 2003/0119869 A1 | 6/2003 | Burrows et al. |
| 2004/0157853 A1 | 8/2004 | Bonnert |
| 2004/0224961 A1 | 11/2004 | Willis et al. |
| 2005/0171345 A1 | 8/2005 | Bonnert et al. |
| 2005/0234077 A1 | 10/2005 | Bonnert et al. |
| 2005/0272750 A1 | 12/2005 | Brough et al. |
| 2006/0100221 A1 | 5/2006 | Bonnert |
| 2006/0111569 A1 | 5/2006 | Bonnert |
| 2007/0142352 A1 | 6/2007 | Bonnert et al. |
| 2007/0282103 A1 | 12/2007 | Butters et al. |

FOREIGN PATENT DOCUMENTS

| | | |
|---|---|---|
| WO | WO 97/22596 | 6/1997 |
| WO | WO 97/30035 | 8/1997 |
| WO | WO 97/32856 | 9/1997 |
| WO | WO 97/40035 | 10/1997 |
| WO | WO 98/08847 | 3/1998 |
| WO | WO 98/13354 | 4/1998 |
| WO | WO 98/25617 | 6/1998 |
| WO | WO 99/02166 | 1/1999 |
| WO | WO 99/04794 | 2/1999 |
| WO | WO 99/17773 | 4/1999 |
| WO | WO 99/36421 | 7/1999 |
| WO | WO 99/51608 | 10/1999 |
| WO | WO 00/08013 | 2/2000 |
| WO | WO 00/09511 | 2/2000 |
| WO | WO 00/38680 | 7/2000 |
| WO | WO 00/39129 | 7/2000 |
| WO | WO 00/40529 | 7/2000 |
| WO | WO 00/41669 | 7/2000 |
| WO | WO 00/45800 | 8/2000 |
| WO | WO 00/59502 | 10/2000 |
| WO | WO 00/76514 | 12/2000 |
| WO | WO 01/19825 | 3/2001 |
| WO | WO 01/25200 | 4/2001 |
| WO | WO 0125242 * | 4/2001 |
| WO | WO 01/58906 | 8/2001 |
| WO | WO 01/66525 | 9/2001 |
| WO | WO 01/92224 | 12/2001 |
| WO | WO 02/04434 | 1/2002 |
| WO | WO 02/08213 | 1/2002 |
| WO | WO 02/083693 | 10/2002 |
| WO | WO 03/024966 | 3/2003 |
| WO | WO 2004/026835 | 1/2004 |
| WO | WO 2004/026880 | 4/2004 |
| WO | WO 2005/033115 | 4/2005 |
| WO | WO 2005/056563 | 6/2005 |
| WO | WO 2005/082865 | 9/2005 |
| WO | WO 2006/064228 | 6/2006 |

OTHER PUBLICATIONS

Berge et. al. (J. of Pharm. Sciences, 1977, pp. 1-19).*
Office Action mailed Oct. 13, 2006 in U.S. Appl. No. 10/528,270.
Response to Office Action filed Apr. 13, 2007 in U.S. Appl. No. 10/528,270.
Office Action mailed Jun. 27, 2007 in U.S. Appl. No. 10/528,270.
Response to Office Action filed Dec. 27, 2007 in U.S. Appl. No. 10/528,270.
Ahmed et al., "Novel synthesis of 1-aryl-9-alkyl-2,3,3a,4,9,9a-hexahydro-1H-pyrrolo[2,3-b]quinoxalines by lithium aluminum hydride reduction of N-phenyl-1-benzimidazolylsuccinimides", CAPLUS 79:92106 (1973), abstract.
Baly et al., "Biological Assays for C-X-C Chemokines", *Methods in Enzymology* 287:69-88 (1997).
Baxter et al., "Hit-to-Lead Studies: The Discovery of Potent, Orally Bioavailable Thiazolopyrimidine CXCR2 Receptor Antagonists", *Bioorg. Med. Chem. Lett.* 16(4):90-963 (2006).
Bodor et al., "Chemical Approaches to Drug Delivery", in: *Encyclopedia of Controlled Drug Delivery* (1999 ed.), pp. 285-298.
CAPLUS, Accession No. 2000:76301, Document No. 132:98128, "Antiinflammatory and analgesic capsules containing betamethasone, vitamin B6, dihydrochlorothiazide and triamterene", 1988.
Chemcats, Accession No. 2001:1442861, "4, 7-Pteridinediamine, 9-phenyl-2-[(phenylmethyl)thio]-," CAS Registry 343347-55-7 (Jul. 1, 2001).
Chemical Abstracts, vol. 54, No. 10, May 1960, Abstract No. 9933f, C. Wayne Noell and Roland K. Robins, "Potential Purine Antagonists XVII. Synthesis of 2-methyl and 2-methylthio-6, 8-disubstituted purines", see formula III when R-SMe, R1=Cl, R2=OH.
Cohen et al., "Cytokine function: A study in biologic diversity", CAPLUS 125:31527 (1996), abstract.
Cowley et al., "Preparation of 1-(3-phenyloxypropyl)piperdine derivatives as opioid receptor ligands", CAPLUS 138:39189 (2002), abstract.
Faubl, "Preparation of 5-Tetrazolyl Groups from Carboxylic Acids. A Sequence Amenable to Sensitive Substrates", *Tetrahedron Letters* 6:491-494 (1979).
Finke et al., "Preparation of piperidinylmethylcyclopentanes as modulators of CCR-5 and/or CCR-3 chemokine receptors", CAPLUS 134:56576 (2000) CAS Listing, 77 answers, abstract.
Fukuda et al., "Preparation of benzotriazole derivatives as cardiovascular agents and antipsychotics", CAPLUS 123:340149 (1995), abstract.
Gavezzotti, "Are Crystal Structures Predictable?", *Acc. Chem. Res.* 27:309-314 (1994).
Gewald et al., "New Synthesis of Substituted 4-Amino-quinazolines and Their Heteroanaloga", *J. prakt. Chem.* 338:206-213 (1996).
Grant, "University of Minnesota—Twin Cities Campus College of Pharmacy, Annual Report", [online] 1999, [retrieve on Feb. 13, 2003]. Retrieved from the internet, http://www.msi.umn.edu/general/Reports/ar99/departments/pharmacy.html.
Grohe et al., "Cycloacylation of Enamines, I.—Synthesis of 2-Thiazolone Derivatives", *Liebigs Ann. Chem.* 1018-1024 (1973).
Kiriasis et al., "Synthesis and Properties of New Pteridine Nucleosides", *Dev. Biochem.* 4:49-53 (1978).
Lee et al., "Characterization of Two High Affinity Human Interleukin-8 Receptors", *J. Biol. Chem.* 267:16283-16287 (1992).
McNaught et al., "IUPAC Compendium of Chemical Terminology, $2^{nd}$ Ed" (1997).
Merritt et al., "Use of fluo-3 to measure cytosolic $Ca^{2+}$ in platelets and neutrophils: Loading cells with the dye, calibration of traces, measurements in the presence of plasma, and buffering of cytosolic $Ca^{2+}$", *Biochem. J.* 269:513-519 (1990).
Murdoch and Finn, "Chemokine receptors and their role in inflammation and infectious diseases", *Blood* 95:3032 (3043 (2000).
Nagahara et al., "Thiazolo[4,5-d]pyrimidine Nucleosides. The Synthesis of Certain 3-β-D-Ribofuranosylthiazolo(4,5-d]pyrimidines as Potential Immunotherapeutic Agents", *J. Med. Chem.* 33:407-415 (1990).
Ott et al., "4-amino-7, 8-dihydro-2-(methylmercapto)-8-β,-D-ribofuranosylpteridin-7-One. Modified Fusion Reaction with Trimethylsilylated Pteridine Derivatives", *Nucl. Acid. Chem.* 2:735-739 (1978).
Ott et al., "Zur Synthese des 4-Amino-7-oxo-7, 8-dihydropteridin-N-8-β-D-ribofuranosids—ein strukturanaloges Nucleosid des Adenosins", *Chem.Ber.* 107:339-361 (1974).
Pachter and Nemeth, "Pteridines. I. Synthesis of Some 6-Alkyl-7-aminopteridines from Nitrosopyrimidines", *J. Org. Chem.* 28:1187-1191 (1963).
Patent Abstracts of Japan, abstract of JP-5-202047 A (Chugai Pharmaceut. Co. Ltd.) Aug. 10, 1993.
Power et al., "Differential Histopathology and Chemokine Gene Expression in Lung Tissues following Respiratory Syncytial Virus (RSV) Challenge of Formalin-Inactivated RSV—or BBG2Na-Immunized Mice", *J. Virol.* 75:12421-12430 (2001).
Sato et al., "Psychotropic Agents. 3. 4-(4-Substituted piperidinyl)-1-(4-flurophenyl)-1-butanones with Potent Neuroleptic Activity," *Journal of Medicinal Chemistry* 21(11):1116-1120 (1978).

Souillac et al., "Characterization of Delivery Systems, Differential Scanning Calorimetry", in: *Encyclopedia of Controlled Drug Delivery* (1999 ed.), pp. 212-227.

Spickett and Timmis, "The Synthesis of Compounds with Potential Anti-folic Acid Activity. Part I. 7-Amino- and 7-Hydroxy-pteridines", *J. Chem. Soc.* pp. 2887-2895 (1954).

Taylor et al., "Molecular Determinants for Recognition of RU 24969 Analogs at Central 5-Hydroxytryptamine Recognition Sites: Use of a Bilinear Function and Substituent Volumes to Describe Steric Fit," *Molecular Pharmacology* 32:42-53 (1988).

Teranishi et al., "Piperidine derivatives and pharmaceutical compositions containing them", CAPLUS 95:132947 (1981), abstract.

Vandenberk et al., "1-(Benzazolylalkyl)piperidines and their salts with acids", CAPLUS 87:23274 (1977), abstract.

Vartanyan et al., "Synthesis and biological activity of 1-substituted benzimidazole and benztriazole derivatives", CAPLUS 98:4503 (1983), abstract.

Vippagunta et al., "Crystalline Solids", *Advanced Drug Delivery Reviews* 48:3-26 (2001).

Weinstock et al., "Pteridines. XII. Structure-Activity Relationships of Some Pteridine Diruetics", *J. Med. Chem.* 11(3):573-579 (1968).

West, "Solid State Chemistry and its applications", Wiley, New York, pp. 358 & 365 (1988).

Wu et al., "Synthesis of Furanonaphthoquinones with Hydroxyamino Side Chains", *J. Nat. Prod.* 62:963-968 (1999).

Traves, et al., "Specific CXC but not CC chemokines cause elevated monocyte migration in COPD: a role for CXCR2," *Journal of Leukocyte Biology*, 2004, 76: 441-450.

* cited by examiner

SUBSTITUTED THIAZOLO[4,5-D]PYRIMIDIN-2(3H)-ONE

CROSS-REFERENCE TO RELATED APPLICATIONS

This application is the national phase application under 35 U.S.C. § 371 of PCT International Application No. PCT/GB2003/003998, filed Sep. 16, 2003, which claims priority to United Kingdom Application Serial No. 0221828.7, filed Sep. 20, 2002.

STATEMENT REGARDING FEDERALLY SPONSORED RESEARCH OR DEVELOPMENT

Not Applicable.

THE NAMES OF THE PARTIES TO A JOINT RESEARCH AGREEMENT

Not Applicable.

INCORPORATION-BY-REFERENCE OF MATERIAL SUBMITTED ON A COMPACT DISC

Not applicable.

The present invention relates to a thiazolopyrimidinone compound, processes and intermediates used in its preparation, pharmaceutical compositions containing it and its use in therapy.

Chemokines play an important role in immune and inflammatory responses in various diseases and disorders, including asthma and allergic diseases, as well as autoimmune pathologies such as rheumatoid arthritis and atherosclerosis. These small secreted molecules are a growing superfamily of 8-14 kDa proteins characterised by a conserved four cysteine motif. At the present time, the chemokine superfamily comprises three groups exhibiting characteristic structural motifs, the Cys-X-Cys (C—X—C), Cys-Cys (C—C) and Cys-$X_3$-Cys (C—$X_3$—C) families. The C—X—C and C—C families have sequence similarity and are distinguished from one another on the basis of a single amino acid insertion between the NH-proximal pair of cysteine residues. The C—$X_3$—C family is distinguished from the other two families on the basis of having a triple amino acid insertion between the NH-proximal pair of cysteine residues.

The C—X—C chemokines include several potent chemoattractants and activators of neutrophils such as interleukin-8 (IL-8) and neutrophil-activating peptide 2 (NAP-2).

The C—C chemokines include potent chemoattractants of monocytes and lymphocytes but not neutrophils. Examples include human monocyte chemotactic proteins 1-3 (MCP-1, MCP-2 and MCP-3), RANTES (Regulated on Activation, Normal T Expressed and Secreted), eotaxin and the macrophage inflammatory proteins 1α and 1β (MIP-1α and MIP-1β).

The C—$X_3$—C chemokine (also known as fractalkine) is a potent chemo attractant and activator of microglia in the central nervous system (CNS) as well as of monocytes, T cells, NK cells and mast cells.

Studies have demonstrated that the actions of the chemokines are mediated by subfamilies of G protein-coupled receptors, among which are the receptors designated CCR1, CCR2, CCR2A, CCR2B, CCR3, CCR4, CCR5, CCR6, CCR7, CCR8, CCR9, CCR10 and CCR11 (for the C—C family); CXCR1, CXCR2, CXCR3, CXCR4 and CXCR5 (for the C—X—C family) and $CX_3CR1$ for the C—$X_3$—C family. These receptors represent good targets for drug development since agents which modulate these receptors would be useful in the treatment of disorders and diseases such as those mentioned above.

BACKGROUND OF THE INVENTION

WO-01/25242 discloses a series of thiazolopyrimidinone compounds useful as CXCR2 antagonists. A compound within the scope of WO-01/25242, but not specifically disclosed therein, has now surprisingly been found to have an improved pharmacological profile when compared with the structurally most similar compounds from WO-01/25242 i.e. Examples 4 and 7.

BRIEF DESCRIPTION OF THE SEVERAL VIEWS OF THE DRAWING(S)

Not applicable.

DETAILED DESCRIPTION OF THE INVENTION

The present invention therefore provides a compound of formula (I) and pharmaceutically acceptable salts or solvates thereof:

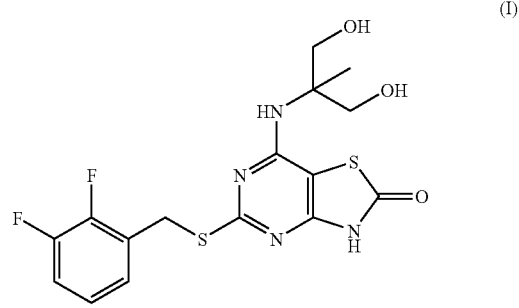

(I)

The compound of formula (I) is capable of existing in tautomeric form. Tautomers and mixtures thereof also form an aspect of the present invention.

According to the invention there is also provided a process for the preparation of compound (I) which comprises reaction of a compound of formula (II):

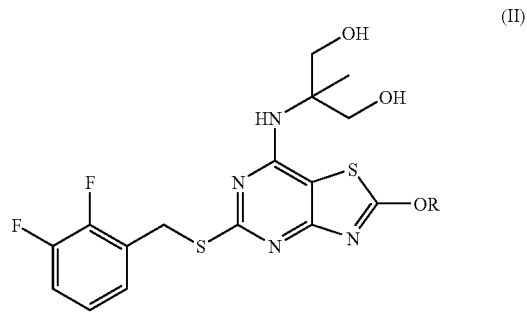

(II)

where R is $C_{1-6}$ alkyl with an acid,
and optionally thereafter: forming a pharmaceutically acceptable salt.

Preferably R is ethyl or methyl, more preferably methyl. Preferably the reaction is carried out using dioxan and HCl. Preferably the compounds of the invention are prepared according to the procedures exemplified herein.

The compound (II) can be prepared from the corresponding compound of formula (III):

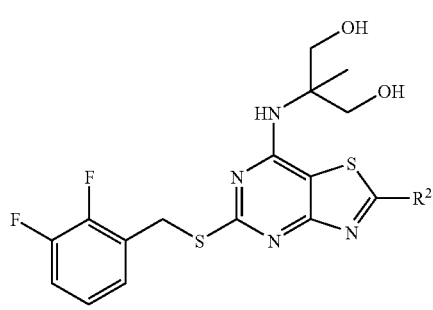
(III)

where $R^2$ is halogen by treating with a compound ROH in the presence of a base. Preferably the compound of formula (III) is treated with sodium methoxide. Preferably $R^2$ is chloro.

Compounds of formula (III) can be prepared using the sequence below:

It will be appreciated by those skilled in the art that in the processes of the present invention certain functional groups such as hydroxyl or amino groups in the starting reagents or intermediate compound may need to be protected by protecting groups. Thus, the preparation of the compound of formula (I) may involve, at an appropriate stage, the removal of one or more protecting groups. The protection and deprotection of functional groups is fully described in 'Protective Groups in Organic Chemistry', edited by J. W. F. McOmie, Plenum Press (1973), and 'Protective Groups in Organic Synthesis', 2nd edition, T. W. Green & P. G. M. Wuts, Wiley-Interscience (1991).

The compound of formula (I) above may be converted to a pharmaceutically acceptable salt or solvate thereof, preferably a basic addition salt such as sodium, potassium, calcium, aluminium, lithium, magnesium, zinc, benzathine, chloroprocaine, choline, diethanolamine, ethanolamine, ethyldiamine, meglumine, tromethamine or procaine, or an acid addition salt such as a hydrochloride, hydrobromide, phosphate, acetate, fumarate, maleate, tartrate, citrate, oxalate, methanesulphonate or p-toluenesulphonate.

The compound of formula (I) has activity as a pharmaceutical, in particular as a modulator of chemokine receptor

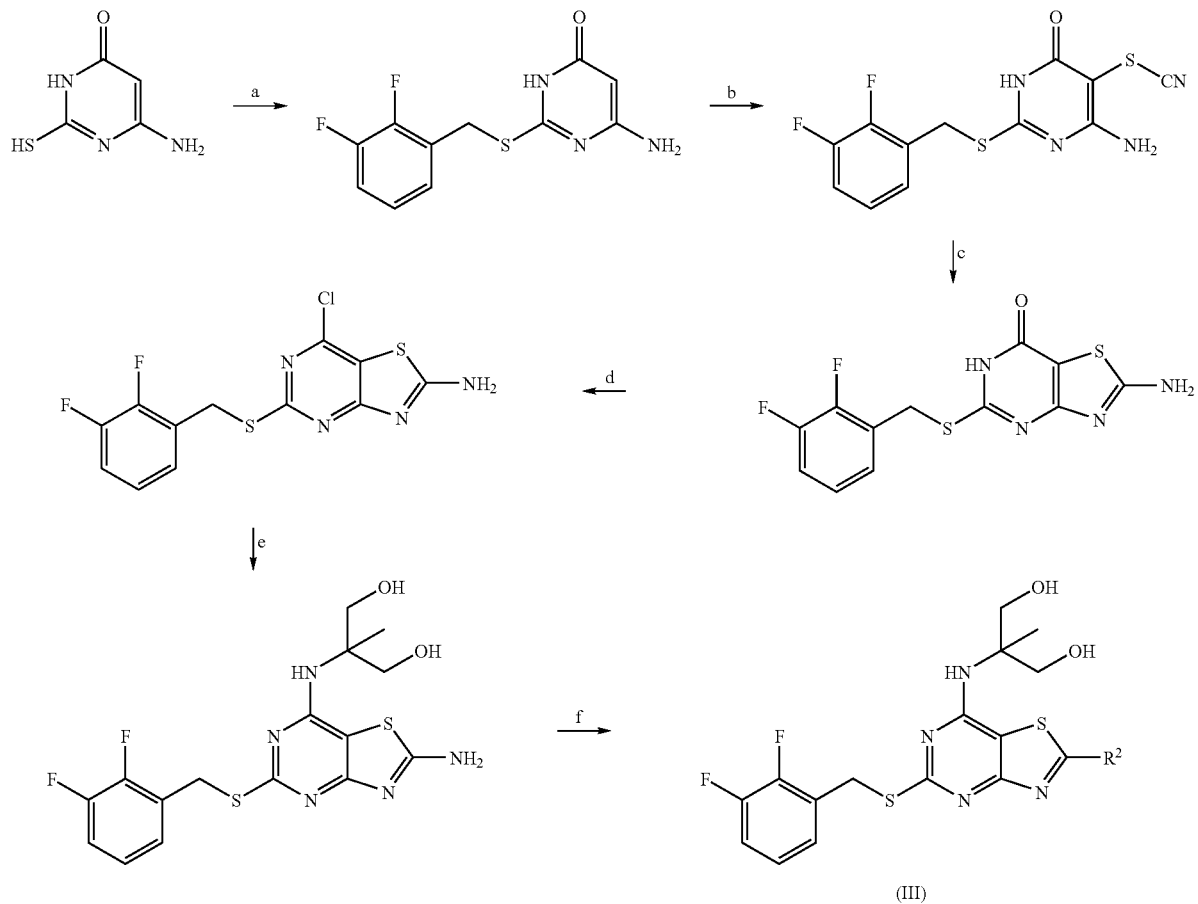

Suitable reagents for steps a to f will be known to those skilled in the art. Preferably steps a to f are carried out as exemplified herein.

The compound of formula (II) is itself believed to be novel and forms a further aspect of the invention.

(especially CXCR2) activity, and may be used in the treatment (therapeutic or prophylactic) of conditions/diseases in human and non-human animals which are exacerbated or caused by excessive or unregulated production of chemokines. Examples of such conditions/diseases include:

(1) (the respiratory tract) obstructive airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;

(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;

(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;

(4) (gastrointestinal tract) Coeliac disease, proctitis, eosinopilic gastro-enteritis, mastocytosis, Crohn's disease; ulcerative colitis, indeterminate colitis, microscopic colitis, inflammatory bowel disease, irritable bowel syndrome, non-inflammatory diarrhea, food-relate allergies which have effects remote from the gut, e.g., migraine, rhinitis and eczema;

(5) (central and peripheral nervous system) Neurodegenerative diseases and dementia disorders, e.g. Alzheimer's disease, amyotrophic lateral sclerosis and other motor neuron diseases, Creutzfeldt-Jacob's disease and other prion diseases, HIV encephalopathy (AIDS dementia complex), Huntington's disease, frontotemporal dementia, Lewy body dementia and vascular dementia; polyneuropathies, e.g. Guillain-Barré syndrome, chronic inflammatory demyelinating polyradiculoneuropathy, multifocal motor neuropathy, plexopathies; CNS demyelination, e.g. multiple sclerosis, acute disseminated/haemorrhagic encephalomyelitis, and subacute sclerosing panencephalitis; neuromuscular disorders, e.g. myasthenia gravis and Lambert-Eaton syndrome; spinal disorders, e.g. tropical spastic paraparesis, and stiff-man syndrome: paraneoplastic syndromes, e.g. cerebellar degeneration and encephalomyelitis; CNS trauma; migraine; and stroke.

(6) (other tissues and systemic disease) Atherosclerosis, Acquired Immunodeficiency Syndrome (AIDS), lupus erythematosus, systemic lupus, erythematosus, Hashimoto's thyroiditis, type I diabetes, nephrotic syndrome, eosinophilia fascitis, hyper IgE syndrome, lepromatous leprosy, and idiopathic thrombocytopenia pupura; post-operative adhesions, and sepsis.

(7) Stroke, subarachnoid haemorrage, re-perfusion injury in the heart, brain, peripheral limbs and other organs.

(8) (allograft rejection) acute and chronic following, for example, transplantation of kidney, heart, liver, lung, bone marrow, skin and cornea; and chronic graft versus host disease;

(9) Cancers, especially non-small cell lung cancer (NSCLC), malignant melanoma, prostate cancer and squamous sarcoma, and tumour metastasis;

(10) Diseases in which angiogenesis is associated with raised CXCR2 chemokine levels (e.g. NSCLC, diabetic retinopathy).

(11) Cystic fibrosis

(12) Burn wounds & chronic skin ulcers

(13) Reproductive Diseases (e.g. Disorders of ovulation, menstruation and implantation, Pre-term labour, Endometriosis)

Thus, the present invention provides a compound of formula (I), or a pharmaceutically-acceptable salt or solvate thereof, as hereinbefore defined for use in therapy.

Preferably the compound of the invention is used to treat diseases in which the chemokine receptor belongs to the CXC chemokine receptor subfamily, more preferably the target chemokine receptor is the CXCR2 receptor, Particular conditions which can be treated with the compound of the invention are rheumatoid arthritis, diseases in which angiogenesis is associated with raised CXCR2 chemokine levels, and COPD. It is preferred that the compound of the invention is used to treat rheumatoid arthritis and respiratory disease.

As a further aspect of the present invention, the compound of formula (I) may have utility as an antagonist of the CX3CR1 receptor. Such a compound is expected to be particularly useful in the treatment of disorders within the central and peripheral nervous system and other conditions characterized by an activation of microglia and/or infiltration of leukocytes (e.g. stroke/ischemia and head trauma).

In a further aspect, the present invention provides the use of a compound of formula (I), or a pharmaceutically acceptable salt or solvate thereof, as hereinbefore defined in the manufacture of a medicament for use in therapy.

In a still further aspect, the present invention provides the use of a compound of formula (I), or a pharmaceutically acceptable salt or solvate thereof, as hereinbefore defined in the manufacture of a medicament for the treatment of human diseases or conditions in which modulation of chemokine receptor activity is beneficial.

In the context of the present specification, the term "therapy" also includes "prophylaxis" unless there are specific indications to the contrary. The terms "therapeutic" and "therapeutically" should be construed accordingly.

The invention still further provides a method of treating a chemokine mediated disease wherein the chemokine binds to a chemokine (especially CXCR2) receptor, which comprises administering to a patient a therapeutically effective amount of a compound of formula (I), or a pharmaceutically acceptable salt or solvate thereof, as hereinbefore defined.

The invention also provides a method of treating an inflammatory disease, especially rheumatoid arthritis, COPD, respiratory disease and psoriasis, in a patient suffering from, or at risk of, said disease, which comprises administering to the patient a therapeutically effective amount of a compound of formula (I), or a pharmaceutically acceptable salt or solvate thereof, as hereinbefore defined.

For the above-mentioned therapeutic uses the dosage administered will, of course, vary with the compound employed, the mode of a distribution, the treatment desired and the disorder indicated.

The compound of formula (I) and pharmaceutically acceptable salts and solvates thereof may be used on their own but will generally be administered in the form of a pharmaceutical composition in which the formula (I) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably from 0.05 to 80% w, still more preferably from 0.10 to 70% w, and even more preferably from 0.10 to 50% w, of active ingredient, all percentages by weight being based on total composition.

The present invention also provides a pharmaceutical composition comprising a compound of formula (I), or a pharmaceutically acceptable salt or solvate thereof, as hereinbefore defined, in association with a pharmaceutically acceptable adjuvant, diluent or carrier.

The invention further provides a process for the preparation of a pharmaceutical composition of the invention which comprises mixing a compound of formula (I), or a pharmaceutically acceptable salt or solvate thereof, as hereinbefore defined, with a pharmaceutically acceptable adjuvant, diluent or carrier.

The pharmaceutical compositions may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally. Preferably the compound of the invention is administered orally.

The invention further relates to combination therapies wherein a compound of formula (1) or a pharmaceutically acceptable salts, solvate or in vivo hydrolysable ester thereof, or a pharmaceutical composition or formulation comprising a compound of formula (1) is administered concurrently or sequentially with therapy and/or an agent for the treatment of any one of asthma, allergic rhinitis, cancer, COPD, rheumatoid arthritis, psoriasis, inflammatory bowel disease, irritable bowel syndrome, ostearthitis or osteoporosis.

In particular, for the treatment of the inflammatory diseases rheumatoid arthritis, psoriasis, inflammatory bowel disease, irritable bowel syndrome, COPD, asthma and allergic rhinitis the compounds of the invention may be combined with agents such as TNF-α inhibitors such as anti-TNF monoclonal antibodies (such as Remicade, CDP-870 and D.sub2.E.sub7.) and TNF receptor immunoglobulin molecules (such as Enbrel.reg.), non-selective COX-1/COX-2 inhibitors (such as piroxicam, diclofenac, propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin), COX-2 inhibitors (such as meloxicam, celecoxib, rofecoxib, valdecoxib and etoricoxib) low dose methotrexate, lefunomide; ciclesonide; hydroxychloroquine, d-penicillamine, auranofin or parenteral or oral gold. For inflammatory bowel disease and irritable bowel disorder further convenient agents include sulphasalazine and 5-ASAs, topical and systemic steroids, immunomodulators and immunosuppressants, antibiotics, probiotics and anti-integrins.

The present invention still further relates to the combination of a compound of the invention together with a leukotriene biosynthesis inhibitor, 5-lipoxygenase (5-LO) inhibitor or 5-lipoxygenase activating protein (FLAP) antagonist such as zileuton; ABT-761; fenleuton; tepoxalin; Abbott-79175; Abbott-85761; N-(5-substituted)-thiophene-2-alkylsulfonamides; 2,6-di-tert-butylphenol hydrazones; methoxytetrahydropyrans such as Zeneca ZD-2138; the compound SB-210661; pyridinyl-substituted 2-cyanonaphthalene compounds such as L-739,010; 2-cyanoquinoline compounds such as L-746,530; indole and quinoline compounds such as MK-591, MK-886, and BAY x 1005.

The present invention still further relates to the combination of a compound of the invention together with a receptor antagonist for leukotrienes LTB.sub4., LTC.sub4., LTD.sub4., and LTE.sub4. selected from the group consisting of the phenothiazin-3-ones such as L-651,392; amidino compounds such as CGS-25019c; benzoxalamines such as ontazolast; benzenecarboximidamides such as BIIL 284/260; and compounds such as zafirlukast, ablukast, montelukast, pranlukast, verlukast (MK-679), RG-12525, Ro-245913, iralukast (CGP 45715A), and BAY x 7195.

The present invention still further relates to the combination of a compound of the invention together with a PDE4 inhibitor including inhibitors of the isoform PDE4D.

The present invention still further relates to the combination of a compound of the invention together with a antihistaminic H.sub1. receptor antagonists such as cetirizine, loratadine, desloratadine, fexofenadine, astemizole, azelastine, and chlorpheniamine.

The present invention still further relates to the combination of a compound of the invention together with a gastroprotective H.sub2. receptor antagonist.

The present invention still relates to the combination of a compound of the invention together with an α.sub1.- and α.sub2.-adrenoceptor agonist vasoconstrictor sympathomimetic agent, such as propylhexedrine, phenylephrine, phenylpropanolamine, pseudoephedrine, naphazoline hydrochloride, oxymetazoline hydrochloride, tetrahydrozoline hydrochloride, xylometazoline hydrochloride, and ethylnorepinephrine hydrochloride.

The present invention still further relates to the combination of a compound of the invention together with anticholinergic agents such as ipratropium bromide; tiotropium bromide; oxitropium bromide; pirenzepine; and telenzepine.

The present invention still further relates to the combination of a compound of the invention together with a β.sub1.-to β.sub4.-adrenoceptor agonists such as metaproterenol, isoproterenol, isoprenaline, albuterol, salbutamol, formoterol, salmeterol, terbutaline, orciprenaline, bitolterol mesylate, and pirbuterol; or methylxanthanines including theophylline and aminophylline; sodium cromoglycate; or muscarinic receptor (M1, M2, and M3) antagonist.

The present invention still further relates to the combination of a compound of the invention together with an insulin-like growth factor type I (IGF-1) mimetic.

The present invention still further relates to the combination of a compound of the invention together with an inhaled glucocorticoid with reduced systemic side effects, such as prednisone, prednisolone, flunisolide, triamcinolone acetonide, beclomethasone dipropionate, budesonide, fluticasone propionate, and mometasone furoate.

The present invention still further relates to the combination of a compound of the invention together with an inhibitor of matrix metalloproteases (MMPs), i.e., the stromelysins, the collagenases, and the gelatinases, as well as aggrecanase; especially collagenase-1 (MMP-1), collagenase-2 (MMP-8), collagenase-3 (MMP-13), stromelysin-1 (MMP-3), stromelysin-2 (MMP-10), and stromelysin-3 (MMP-11) and MMP-12.

The present invention still further relates to the combination of a compound of the invention together with other modulators of chemokine receptor function such as CCR1, CCR2, CCR2A, CCR2B, CCR3, CCR4, CCR5, CCR6, CCR7, CCR8, CCR9, CCR10 and CCR11 (for the C—C family); CXCR1, CXCR3, CXCR4 and CXCR5 (for the C—X—C family) and $CX_3CR1$ for the $C—X_3—C$ family.

The present invention still further relates to the combination of a compound of the invention together with antiviral agents such as Viracept, AZT, aciclovir and famciclovir, and antisepsis compounds such as Valant.

The present invention still further relates to the combination of a compound of the invention together with cardiovascular agents such as calcium channel blockers, lipid lowering agents such as statins, fibrates, beta-blockers, Ace inhibitors, Angiotensin-2 receptor antagonists and platelet aggregation inhibitors.

The present invention still further relates to the combination of a compound of the invention together with CNS agents such as antidepressants (such as sertraline), anti-Parkinsonian drugs (such as deprenyl, L-dopa, Requip, Mirapex, MAOB inhibitors such as selegine and rasagiline, comP inhibitors such as Tasmar, A-2 inhibitors, dopamine reuptake inhibitors, NMDA antagonists, Nicotine agonists, Dopamine agonists and inhibitors of neuronal nitric oxide synthase), and anti-Alzheimer's drugs such as donepezil, tacrine, COX-2 inhibitors, propentofylline or metryfonate.

The present invention still further relates to the combination of a compound of the invention together with (i) tryptase inhibitors; (ii) platelet activating factor (PAF) antagonists; (iii) interleukin converting enzyme (ICE) inhibitors; (iv) IMPDH inhibitors; (v) adhesion molecule inhibitors including VLA-4 antagonists; (vi) cathepsins; (vii) MAP kinase inhibitors; (viii) glucose-6 phosphate dehydrogenase inhibitors; (ix) kinin-B.sub1.- and B.sub2.-receptor antagonists; (x) anti-gout agents, e.g., colchicine; (xi) xanthine oxidase inhibitors, e.g., allopurinol; (xii) uricosuric agents, e.g., probenecid, sulfinpyrazone, and benzbromarone; (xiii) growth hormone secretagogues; (xiv) transforming growth factor (TGFβ); (xv) platelet-derived growth factor (PDGF); (xvi) fibroblast growth factor, e.g., basic fibroblast growth factor (bFGF); (xvii) granulocyte macrophage colony stimulating factor (GM-CSF); (xviii) capsaicin cream; (xix) Tachykinin NK.sub1. and NK.sub3. receptor antagonists selected from the group consisting of NKP-608C; SB-233412 (talnetant); and D-4418; (xx) elastase inhibitors selected from the group consisting of UT-77 and ZD-0892; (xxi) TNFδ converting enzyme inhibitors (TACE); (xxii) induced nitric oxide synthase inhibitors (iNOS) or (xxiii) chemoattractant receptor-homologous molecule expressed on TH2 cells, (CRTH2 antagonists).

The compounds of the present invention may also be used in combination with osteoporosis agents such as roloxifene, droloxifene, lasofoxifene or fosomax and immunosuppressant agents such as FK-506, rapamycin, cyclosporine, azathioprine, and methotrexate.

The compounds of the invention may also be use in combination with existing therapeutic agents for the treatment of osteoarthritis. Suitable agents to be used in combination include standard non-steroidal anti-inflammatory agents (hereinafter NSAID's) such as piroxicam, diclofenac propionic acids such as naproxen, flubiprofen, fenoprofen, ketoprofen and ibuprofen, fenamates such as mefenamic acid, indomethacin, sulindac, apazone, pyrazolones such as phenylbutazone, salicylates such as aspirin, COX-2 in inhibitors such as celecoxib, valdecoxib, rofecoxib and etoricoxib, analgesics and intraarticular therapies such as corticosteroids and hyaluronic acids such as hyalgan and synvisc and P2X7 receptor antagonists.

The compounds of the invention can also be used in combination with existing therapeutic agents for the treatment of cancer. Suitable agents to be used in combination include:

(i) antiproliferative/antineoplastic drugs and combinations thereof, as used in medical oncology, such as alkylating agents (for example cis-platin, carboplatin, cyclophosphamide, nitrogen mustard, melphalan, chlorambucil, busulphan and nitrosoureas); antimetabolites (for example antifolates such as fluoropyrimidines like 5-fluorouracil and tegafur, raltitrexed, methotrexate, cytosine arabinoside, hydroxyurea, gemcitabine and paclitaxel (Taxol®); antitumour antibiotics (for example anthracyclines like adriamycin, bleomycin, doxorubicin, daunomycin, epirubicin, idanibicin, mitomycin-C, dactinomycin and mithramycin); antimitotic agents (for example vinca alkaloids like vincristine, vinblastine, vindesine and vinorelbine and taxoids like taxol and taxotere); and topoisomerase inhibitors (for example epipodophyllotoxins like etoposide and teniposide, amsacrine, topotecan and camptothecin);

(ii) cytostatic agents such as antioestrogens (for example tamoxifen, toremifene, raloxifene, droloxifene and iodoxyfene), oestrogen receptor down regulators (for example fulvestrant), antiandrogens (for example bicalutamide, flutamide, nilutamide and cyproterone acetate), LHRH antagonists or LHRH agonists (for example goserelin, leuprorelin and buserelin), progestogens (for example megestrol acetate), aromatase inhibitors (for example as anastrozole, letrozole, vorazole and exemestane) and inhibitors of 5α-reductase such as finasteride;

(iii) Agents which inhibit cancer cell invasion (for example metalloproteinase inhibitors like marimastat and inhibitors of urokinase plasminogen activator receptor function);

(iv) inhibitors of growth factor function, for example such inhibitors include growth factor antibodies, growth factor receptor antibodies (for example the anti-erbb2 antibody trastuzumab [Herceptin™] and the anti-erbb1 antibody cetuximab [C225]), farnesyl transferase inhibitors, tyrosine kinase inhibitors and serine/threonine kinase inhibitors, for example inhibitors of the epidermal growth factor family (for example EGFR family tyrosine kinase inhibitors such as N-(3-chloro-4-fluorophenyl)-7-methoxy-6-(3-morpholinopropoxy)quinazolin-4-amine (gefitinib, AZD1839), N-(3-ethynylphenyl)-6,7-bis(2-methoxyethoxy)quinazolin-4-amine (erlotinib, OSI-774) and 6-acrylamido-N-(3-chloro-4-fluorophenyl)-7-(3-morpholinopropoxy)quinazolin-4-amine (CI 1033)), for example inhibitors of the platelet-derived growth factor family and for example inhibitors of the hepatocyte growth factor family;

(v) antiangiogenic agents such as those which inhibit the effects of vascular endothelial growth factor, (for example the anti-vascular endothelial cell growth factor antibody bevacizumab [Avastin™], compounds such as those disclosed in International Patent Applications WO 97/22596, WO 97/30035, WO 97/32856 and WO 98/13354) and compounds that work by other mechanisms (for example linomide, inhibitors of integrin αvβ3 function and angiostatin);

(vi) vascular damaging agents such as Combretastatin A4 and compounds disclosed in International Patent Applications WO 99/02166, WO00/40529, WO 00/41669, WO01/92224, WO02/04434 and WO02/08213;

(vii) antisense therapies, for example those which are directed to the targets listed above, such as ISIS 2503, an anti-ras antisense;

(viii) gene therapy approaches, including for example approaches to replace aberrant genes such as aberrant p53 or aberrant BRCA1 or BRCA2, GDEPT (gene-directed enzyme pro-drug therapy) approaches such as those using cytosine deaminase, thymidine linase or a bacterial nitroreductase enzyme and approaches to increase patient tolerance to chemotherapy or radiotherapy such as multi-drug resistance gene therapy; and (ix) immunotherapy approaches, including for example ex-vivo and in-vivo approaches to increase the immunogenicity of patient tumour cells, such as transfection with cytokines such as interleukin 2, interleukin 4 or granulocyte-macrophage colony stimulating factor, approaches to decrease T-cell anergy, approaches using transfected immune cells such as cytokine-transfected dendritic cells, approaches using cytokine-transfected tumour cell lines and approaches using anti-idiotypic antibodies.

The invention will now be further illustrated by reference to the following examples. In the examples the Nuclear Magnetic Resonance (NMR) spectra were measured on a Varian Unity Inova 300 or 400 MHz spectrometer and the Mass Spectrometry (MS) spectra measured on an Agilent MSD spectrometer Where necessary, the reactions were performed under an inert atmosphere of either nitrogen. Chromatography was generally performed using Matrex Silica 60® (35-70 micron) or Prolabo Silica gel 60® (35-70 micron) suitable for flash silica gel chromatography. High performance liquid-chromatography purification was performed using a Gilson Auto-Purification System. The abbreviations m.p. and DMSO used in the examples stand for melting point and dimethyl sulphoxide respectively. Compounds were named using ACD/labs-6.0 naming programme.

EXAMPLE 1

5-[[(2,3-Difluorophenyl)methyl]thio]-7-[[2-hydroxy-1-(hydroxymethyl) 1 methylethyl]amino]-thiazolo[4,5-d]pyrimidin-2(3H)-one a) 6-Amino-2-[[(2,3-difluorophenyl)methyl]thio]-4(3H)-pyrimidinone 4-Amino-6-hydroxy-2-mercaptopyrimidine monohydrate (7.1 g) was added portion wise to a stirred suspension of 60% sodium hydride (2.4 g) in dry N,N-dimethylformamide (70 ml). After 1 hour a solution of 2,3-Difluorobenzyl bromide (10 g) in dry N,N-dimethylformamide (10 ml) was added. Stirred over weekend at room temperature. Poured on to ice/water and the precipitate was collected by filtration to give 9.6 g of product. 81% yield.
MS (APCI) (+ve) 270 (M+H, 94%)

b) 4Amino-2-[[(2,3-difluorophenyl)methyl]thio]-1,6-dihydro-6-oxo-5-pyrimidinyl ester thiocyanic acid The product from step (a) (28 g) and potassium thiocyanate (40.5 g) in N,N-dimethylformamide (583 ml) were heated together at 65° C. Pyridine (14.5 ml) was added and the solution cooled to 5° C. Bromine (5.0 ml) was added slowly and the reaction mixture stirred for 2 hours at 5-10° C. The reaction mixture was poured onto ice water (4200 ml), stirred for 1 hour and the solid was collected by filtration, washed with water and ether, to give 24 g of product. 70% yield.
MS (APCI) (+ve) 327 (M+H)

c) 2-Amino-5-[[(2,3-difluorophenyl)methyl]thio]-thiazolo[4,5-d]pyrimidin-7(6H)-one A mixture of the product from step (b) (12.1 g), N,N-dimethylformamide (70 ml) and water (20 ml) was heated to 120° C. for 24 hours. A colourless solid precipitated from the solution, which was allowed to cool, and the solid collected by filtration to give 8.3 g of product. 70% yield.
MS (APCI) (+ve) 327 (M+H)

d) 7-Chloro-5-[[(2,3-difluorophenyl)methyl]thio]-thiazolo[4,5-d]pyrimidin-2-amine The product of step (c) (10.0 g) was suspended in phosphoryl chloride (55 ml). N,N-dimethylaniline (5.5 ml) added slowly and reaction mixture heated at reflux for 2 hours. Allowed to cool, then poured on to ice with vigorous stirring; temperature was not allowed to go above 45° C. (ice added). After approximately 20 minutes the temperature stabilized at 30° C. The solid that formed was collected by filtration and washed with water. Purified by column chromatography (EtOAc to 5% MeOH in EtOAc) to give 3.34 g of product. 31% yield.
MS: APCI (+ve) 345 (M+H)

e) 2-[[2-Amino-5-[[(2,3-difluorophenyl)methyl]thio]thiazolo[4,5-d]pyrimidin-7-yl]amino]-2-methyl-1,3-propanediol The product from step (d) (1.5 g) was suspended in NMP (10 ml), then Hunigs base (1.5 ml) and 2-Amino-2-methyl-propanediol (1.37 g) added. Reaction mixture heated to 110° C. under $N_2$ for 4 hrs. A further aliquot of 2-Amino-2-methylpropanediol (0.685 g) was added and mixture heated at 110° C. for 5 hrs. Mixture poured in to water (400 ml) and solid was collected by filtration. Purified by column chromatography (EtOAc: Methanol (95:5)) to give 0.756 g of product. 42% yield.
MS: APCI (+ve) 414 (M+H)

f) 2-[[2-Chloro-5-[[(2,3-difluorophenyl)methyl]thio]thiazolo[4,5-d]pyrimidin-7-yl]amino]-2-methyl-1,3-propanediol The product from step (e) (0.485 g) was suspended in conc.HCl (18 ml) which was then cooled to 15° C. A mixture of water (15 ml) and acetonitrile (25 ml) added to give a solution. Cooled to 5° C. and a solution of sodium nitrite (0.162 g) in water (1 ml) added drop-wise. Stirred at 5° C. for several hours then allowed to warm overnight. Solution cooled to −10° C. and neutralized with ammonia, then concentrated in vacuo. The yellow precipitate was collected by filtration and washed with water. Dried in vacuo to give 0.339 g of product. 67% yield.
MS: APCI (+ve) 433 (M+H)

g) 2-[[5-[[(2,3-Difluorophenyl)methyl]thio]-2-methoxythiazolo[4,5-d]pyrimidin-7-yl]amino]-2-methyl-1,3-propanediol The product from step (f) (0.339 g) was suspended in methanol (32 ml). Potassium hydroxide (0.088 g) added and mixture stirred at 50° C. for 20 minutes. Neutralised with 2N HCl and solvents removed in vacuo to give an orange residue. Water added to remove inorganics and the yellow solid was collected by filtration to give 0.3 g of desired product. 90% yield.
MS: APCI (+ve) 429 (M+H)

h) 5-[[(2,3-Difluorophenyl)methyl]thio]-7-[[2-hydroxy-1-(hydroxymethyl)-1-methylethyl]amino]-thiazolo[4,5-d]pyrimidin-2(3H)-one The product from step (g) (0.3 g) was suspended in a mixture of dioxan (50 ml) and conc.HCl (1 ml). Water (1 ml) was added and the resultant solution heated at 60° C. for 12 hours. Allowed to stand over weekend. Solvents removed in vacuo and residue taken up in water. Yellow precipitate collected by filtration and washed with water. Purified using prep. Hplc Acetonitrile: 0.1% ammonium acetate (90:10 to 95:5) over 25 minutes to give 0.063 g of the desired product. 22% yield.
MS: APCI (+ve) 415 (M+H)
$^1$H NMR: δ (DMSO) 1.25 (3H, s), 3.54-3.66 (4H, m), 4.39 (2H, s), 4.65-4.69 (2H, t), 6.34 (1H, s), 7.12-7.20 (1H, m), 7.29-7.41 (2H, m), 12.43 (1H, s). mp 230-233° C.

EXAMPLE 2

5-[[(2,3-Difluorophenyl)methyl]thio]-7-[[2-hydroxy-1-(hydroxymethyl)-1-methylethyl]amino]-thiazolo[4,5-d]pyrimidin-2(3H)-one, monosodium salt The product from Example 1, step (h) (0.87 g) was suspended in water (80 ml), 1.0M sodium hydroxide (3.0 ml) added, then methanol (15 ml), and the mixture heated on a steam bath. When dissolution was almost complete, the mixture was filtered hot and the filtrate chilled overnight to give a fluffy white precipitate after filtration. This was dried in a vacuum oven overnight at 50° C. (0.60 g).

MS: APCI (+ve) 415 (M+H)

$^1$H NMR: δ (DMSO) 1.23 (3H, s), 3.47-3.58 (4H, m), 4.37 (2H, s), 4.94 (2H, t), 5.29 (1H, s), 7.14 (1H, m), 7.31 (1H, m), 7.35 (1H, m). mp 238° C. (dec.)

Pharmacological Data

Ligand Binding Assay

[$^{125}$I]IL-8 (human, recombinant) was purchased from Amersham, U.K. with a specific activity of 2,000 Ci/mmol. All other chemicals were of analytical grade. High levels of hrCXCR2 were expressed in HEK 293 cells (human embryo kidney 293 cells ECACC No. 85120602) (Lee et al. (1992) *J. Biol. Chem.* 267 pp 16283-16291). hrCXC2 cDNA was amplified and cloned from human neutrophil mRNA. The DNA was cloned into PCRScript (Stratagene) and clones were identified using DNA. The coding sequence was subcloned into the eukaryotic expression vector RcCMV (Invitrogen). Plasmid DNA was prepared using Quiagen Megaprep 2500 and transfected into HEK 293 cells using Lipofectamine reagent (Gibco BRL). Cells of the highest expressing clone were harvested in phosphate-buffered saline containing 0.2% (w/v) ethylenediaminetetraacetic acid (EDTA) and centrifuged (200 g, 5 min.). The cell pellet was resuspended in ice cold homogenisation buffer [10 mM HEPES (pH 7.4), 1 mM dithiothreitol, 1 mM EDTA and a panel of protease inhibitors (1 mM phenyl methyl sulphonyl fluoride, 2 µg/ml soybean trypsin inhibitor, 3 mM benzamidine, 0.5 µg/ml leupeptin and 100 µg/ml bacitracin)] and the cells left to swell for 10 minutes. The cell preparation was disrupted using a hand held glass mortar/PTFE pestle homogeniser and cell membranes harvested by centrifugation (45 minutes, 100,000 g, 4° C.). The membrane preparation was stored at −70° C. in homogenisation buffer supplemented with Tyrode's salt solution (137 mM NaCl, 2.7 mM KCl, 0.4 mM NaH$_2$PO$_4$), 0.1%(w/v) gelatin and 10%(v/v) glycerol. All assays were performed in a 96-well MultiScreen 0.45 µm filtration plates (Millipore, U.K.). Each assay contained ~50 pM [$^{125}$I]IL-8 and membranes (equivalent to ~200,000 cells) in assay buffer [Tyrode's salt solution supplemented with 10 mM HEPES (pH 7.4), 1.8 mM CaCl$_2$, 1 mM MgCl$_2$, 0.125 mg/ml bacitracin and 0.1%(w/v) gelatin]. In addition, a compound of formula (I) according to the Examples was pre-dissolved in DMSO and added to reach a final concentration of 1% (v/v) DMSO. The assay was initiated with the addition of membranes and after 1.5 hours at room temperature the membranes were harvested by filtration using a Millipore MultiScreen vacuum manifold and washed twice with assay buffer (without bacitracin). The backing plate was removed from the MultiScreen plate assembly, the filters dried at room temperature, punched out and then counted on a Cobra γ-counter. The compound of formula (I) has an IC$_{50}$ value of less than (<) 10 µM.

Intracellular Calcium Mobilisation Assay

Human nutrophils were prepared from EDTA-treated peripheral blood, as previously described (Baly et al. (1997) Methods in Enzymology 287 pp 70-72), in storage buffer [Tyrode's salt solution (137 mM NaCl, 2.7 mM KCl, 0.4 mM NaH$_2$PO$_4$) supplemented with 5.7 mM glucose and 10 mM HEPES (pH 7.4)].

The chemokine GROα (human, recombinant) was purchased from R&D Systems (Abingdon, U.K.). All other chemicals were of analytical grade. Changes in intracellular free calcium were measured fluorometrically by loading neutrophils with the calcium sensitive fluorescent dye, fluo-3, as described previously (Merritt et al. (1990) Biochem. J. 269, pp513-519). Cells were loaded for 1 hour at 37° C. in loading buffer (storage buffer with 0.1% (w/v) gelatin) containing 5 µM fluo-3 AM ester, washed with loading buffer and then resuspended in Tyrode's salt solution supplemented with 5.7 mM glucose, 0.1% (w/v) bovine serum albumin (BSA), 1.8 mM CaCl$_2$ and 1 mM MgCl$_2$. The cells were pipetted into black walled, clear bottom, 96 well micro plates (Costar, Boston, U.S.A.) and centrifuged (200 g, 5 minutes, room temperature).

A compound of formula (I) according to the Examples was pre-dissolved in DMSO and added to a final concentration of 0.1% (v/v) DMSO. Assays were initiated by the addition of an A$_{50}$ concentration of GROα and the transient increase in fluo-3 fluorescence ($\lambda_{Ex}$=490 nm and $\lambda_{Em}$=520 nm) monitored using a FLIPR (Fluorometric Imaging Plate Reader, Molecular Devices, Sunnyvale, U.S.A.).

The compound of formula (I) was tested and found to be an antagonist of the CXCR2 receptor in human neutrophils.

The invention claimed is:

1. A monosodium salt of the compound of formula (I):

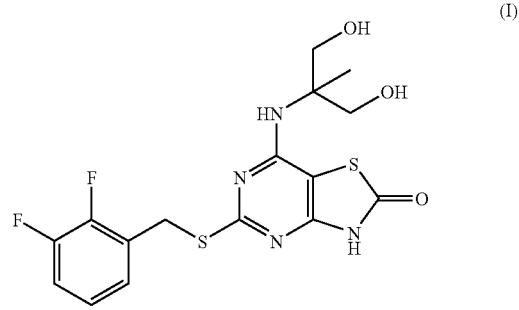

(I)

2. A process for the preparation of the monosodium salt of a compound of formula (I) of claim 1, which comprises reaction of a compound of formula (II):

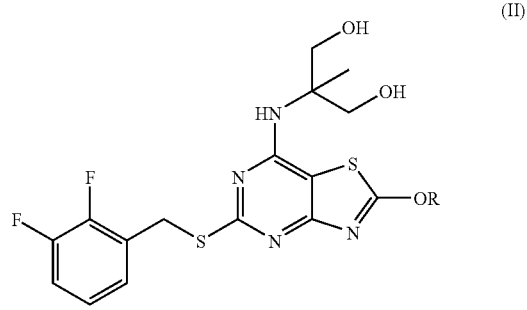

(II)

where R is C$_{1-6}$ alkyl with an acid, and thereafter forming a monosodium salt.

3. A pharmaceutical composition comprising the monosodium salt of the compound of Formula I of claim 1 and a pharmaceutically acceptable adjuvant, diluent, or carrier.

* * * * *

UNITED STATES PATENT AND TRADEMARK OFFICE
CERTIFICATE OF CORRECTION

PATENT NO. : 7,585,867 B2  Page 1 of 1
APPLICATION NO. : 10/528316
DATED : September 8, 2009
INVENTOR(S) : Roger Victor Bonnert It is certified that error appears in the above-identified patent and that said Letters Patent is hereby corrected as shown below:

Column 8, line 3, please delete "LTB.sub4." and insert --$LTB_4$-- therefor;

Column 8, line 3, please delete "LTC.sub4." and insert --$LTC_4$-- therefor;

Column 8, lines 3-4, please delete "LTD.sub4." and insert --$LTD_4$-- therefor;

Column 8, line 4, please delete "LTE.sub4." and insert --$LTE_4$-- therefor;

Column 8, line 16, please delete "H.sub1." and insert --$H_1$-- therefor;

Column 8, line 21, please delete "H.sub2." and insert --$H_2$-- therefor;

Column 8, line 23, please delete "α.sub1." and insert --$\alpha_1$-- therefor;

Column 8, line 24, please delete "α.sub2." and insert --$\alpha_2$-- therefor;

Column 8, line 35, please delete "β.sub1." and insert --$\beta_1$-- therefor;

Column 8, line 36, please delete "β.sub4." and insert --$\beta_4$-- therefor;

Column 9, line 26, please delete "β.sub1." and insert --$\beta_1$-- therefor;

Column 9, line 26, please delete "β.sub2." and insert --$\beta_2$-- therefor.

Signed and Sealed this

Fifteenth Day of December, 2009

David J. Kappos
*Director of the United States Patent and Trademark Office*